United States Patent [19]
Lee et al.

[11] Patent Number: 5,205,154
[45] Date of Patent: Apr. 27, 1993

[54] APPARATUS AND METHOD FOR SIMULTANEOUS SUPERCRITICAL FLUID EXTRACTION AND GAS CHROMATOGRAPHY

[75] Inventors: Milton L. Lee, Pleasant Grove; Paul B. Farnsworth, Orem; Zaiyou Liu, Provo, all of Utah

[73] Assignee: Brigham Young University, Provo, Utah

[21] Appl. No.: 786,252

[22] Filed: Nov. 1, 1991

[51] Int. Cl.$^5$ ............................................. G01N 30/30
[52] U.S. Cl. .................................... 73/23.35; 73/23.42
[58] Field of Search ................. 73/23.35, 23.36, 23.41, 73/23.42, 23.25

[56] References Cited

U.S. PATENT DOCUMENTS

| | | | |
|---|---|---|---|
| 4,845,985 | 7/1989 | Berger | 73/23.25 |
| 4,982,597 | 1/1991 | Berger | 73/23.25 |
| 5,031,448 | 7/1991 | Saito | 73/23.35 X |
| 5,065,614 | 11/1991 | Hartman et al. | 73/23.35 |
| 5,081,871 | 1/1992 | Glaser | 73/863.23 |

FOREIGN PATENT DOCUMENTS

| | | | |
|---|---|---|---|
| 8747 | 1/1985 | Japan | 73/23.35 |
| 1550415 | 3/1990 | U.S.S.R. | 73/23.35 |
| 9103719 | 3/1991 | World Int. Prop. O. | 73/23.35 |

OTHER PUBLICATIONS

Jentoft, R. E. et al. *Apparatus for Supercritical Fluid Chromatography with Carbon Dioxide as the Mobile Phase* in Analy. Chem. vol. 44, No. 4, Apr. 1972, pp. 681–686.

*Primary Examiner*—Hezron E. Williams
*Assistant Examiner*—Joseph W. Roskos
*Attorney, Agent, or Firm*—Thorpe, North & Western

[57] ABSTRACT

A system and method for carrying out supercritical fluid extraction and gas chromatography simultaneously. Sample substances contained in solid (or liquid) matrices are extracted by means of supercritical fluid extraction and carried directly onto a thermal desorption modulator which functions as an interface between the extraction and chromatography systems. Analytes carried by the supercritical fluid are retained in the modulator while the fluid passes through during the cool cycle of the modulator. A thermal pulse raises the temperature of the modulator and releases retained substances, serving as a sharp injection of such substances into a fast separating column to provide high-speed separations. A complete chromatogram with reasonable resolution is generated within a few seconds time period. Thermal modulation signals at a fixed time interval are so chosen that the consequent chromatograms do not interfere with one another. A series of high-speed chromatograms are generated during one extraction, and the extraction and the chromatography are carried out simultaneously. Assemble signal averaging provides a higher signal to noise ratio. Segmented signal averaging of a number of consecutive chromatograms generated from one extraction is similar to off-line fraction collection, but the speed of analysis is substantially enhanced without sacrificing analytical accuracy.

22 Claims, 7 Drawing Sheets

APPARATUS AND METHOD FOR SIMULTANEOUS SUPERCRITICAL FLUID EXTRACTION AND GAS CHROMATOGRAPHY

This invention was made with Government support under Assistance Agreement R-815574-01-0 by the United States Environmental Protection Agency. The Government has certain rights in this invention.

DISCUSSION OF BACKGROUND AND PRIOR ART

This invention is drawn to a method and apparatus for the simultaneous supercritical fluid extraction (SFE) of analytes from a solid matrix and separation and analysis of such analytes by gas chromatography (GC). More particularly, this invention is drawn to a system for the simultaneous supercritical fluid extraction of samples from a solid matrix, sequentially absorbing such samples into a stationary phase in a thermal desorption modulator (TDM), and then releasing such samples at timed intervals into a gas chromatography column as a sharp concentration pulse by thermal desorption thereby allowing a set of high speed chromatograms, sampled from the extraction stream, to be generated while the SFE is proceeding.

Supercritical fluid extraction (SFE) is a method commonly used for sample preparation before analysis The fundamental mechanism of isolating chemical substances of interest from a matrix is based on the solubility of the substance in the extracting fluid. Since viscosities and solute diffusivities of supercritical fluids are similar to those of gases, and their solvating properties approach those of liquids, supercritical fluid extraction can be more efficient and faster than conventional liquid extraction because of more rapid mass transfer and better penetration into the sample matrix. The ease of solvent removal and low extraction temperature are important advantages of SFE when using fluids such as supercritical $CO_2$.

Since analytically useful supercritical fluids usually have low boiling points and sample concentration can be easily achieved by reducing the pressure, on-line coupling of SFE with chromatographic methods should provide easy and reliable sample preparation and analysis Although many attempts have been made to couple supercritical fluid extraction to various chromatographic techniques, none of the methods reported have been successful in carrying out supercritical fluid extraction and chromatographic analysis simultaneously.

Stahl and co-workers coupled supercritical fluid extraction to thin-layer chromatography (TLC) and studied the solubility behavior of various compounds in supercritical carbon dioxide (Stahl et al., *Fresenius Z. Anal. Chem.* 1976, 280, 99–104). With this apparatus, the extracted substances were deposited on the TLC plate during extraction. However, chromatographic analysis was not started until the extraction was completed.

Coupling of supercritical fluid extraction to high performance liquid chromatography (HPLC) was first reported by Unger et al. (Unger et al., *J. Chromatogram* 1983, 282. 519–526), and later by others. In general, the system consisted of a constant-pressure pump to transfer the $CO_2$ to a heated vial containing the sample, an injection valve and an analytical column. The injection loop was first loaded with the extracted substances. The chromatographic analysis then started after injection of the contents of the loop into the front of the analytical column.

Coupling of SFE to capillary supercritical fluid chromatography (SFC) was initially reported by Gmur et al. (Gmur et al., *J. Chromatogr.* 1987, 388, 143–150), and later by others (Levy et al., *J. Chromatogr. Sci.* 1989, 27, 341–346). Interfacing between SFE and SFC was generally achieved by using either a sample injection valve or by cryogenically trapping the extracted sample onto the column head. The extraction and chromatographic analysis were carried out sequentially Hawthorne et al. were the first and the leading investigators in coupling supercritical fluid extraction to gas chromatography (GC) (Hawthorne et al., *J. Chromatogr. Sci.*, 1986, 24, 258–264). This technique was also demonstrated by many other investigators such as Levy et al. and Wright et al. (Levy et al., *J. High Result. Chromatogr.*, 1990, 13, 418–421; et al., *Anal. Chem.*, 1987, 59, 640–644). Since supercritical fluids decompress into gases under typical GC conditions, several interfaces based on standard GC injectors such as split/-splitless injectors, programmed temperature vaporizer injectors, and cold trap injection systems have been described in the literature. As an alternative method, the extractant can be directly transferred onto the column through an on-column injection port. These methods are time consuming because the extraction and chromatography are carried out stepwise. Quantitative analysis depends on both completeness of the extraction and quantitative sample transfer. Furthermore, losing of lower molecular weight components during extraction, and peak shape deterioration for the components are problems commonly encountered in the coupled SFE/GC systems referenced in the prior art.

Using an on-column thermal desorption modulator for sample injection in GC has been reported by Phillips et al. (Phillips et al., *J. Chromatogr. Sci.*, 1986, 24, 396–399). The device was a short section of the analytical column, configured such that the section temperature could be independently controlled apart from the rest of the column. A concentration pulse served as an injection and was generated by a thermal pulse which released retained substances. Thermal modulation, as an interface between SFE and SFC, was demonstrated by Mitra (Mitra et al., *J. Chromatogr. Sci.*, 1990, 28, 182–185). Using an on-column thermal modulator for sample transfer between gas chromatographic columns was demonstrated by Liu et al. (Liu et al., *J. Chromatogr. Sci.*, 1991, 29, 227–231).

While certain components utilized in the present invention are to be found in the prior art as referenced above, no application was found for the use of a thermal modulator as an interface between supercritical fluid extraction and gas chromatography to allow integration of these systems and achieve the simultaneous performance of the two in the extraction and analysis of samples.

OBJECTS AND BRIEF SUMMARY OF THE INVENTION

It is, therefore, a primary object of this invention to provide a system which allows implementation of the simultaneous use of supercritical fluid extraction and gas chromatography by means of thermal modulation, high-speed separation, and on-line coupling.

Another object of the invention is to provide the means of rapid on-line analysis of solid samples by eliminating sample collection, cleanup, concentration, and refocusing steps previously required in the prior art when combining supercritical fluid extraction and gas chromatography.

It is a further object of the invention to provide accurate measurement or close monitoring of dynamic supercritical fluid extraction processes for each individual component of interest coupled with simultaneous gas chromatographic analysis.

It is still a further object of the invention to utilize thermal modulation of supercritical fluid extracted analytes to permit efficient sample transfer, high-speed chromatography, and rapid analysis.

These and other objects may be accomplished by means of an apparatus which carries out supercritical fluid extraction and gas chromatography simultaneously. Sample substances contained in solid (or liquid) matrices are extracted by means of supercritical fluid extraction and carried directly onto a thermal desorption modulator. This modulator works as an interface between the extraction and chromatography systems. Analytes carried by the supercritical fluid are retained in the modulator while the fluid passes through during the cool cycle of the modulator. A thermal pulse raises the temperature of the modulator and releases retained substances, serving as a sharp injection of such substances into the separating column. A fast column is used to provide high-speed separations. A complete chromatogram with reasonable resolution can be generated within a time period as short as a few seconds. Thermal modulation signals at a fixed time interval are so chosen that the consequent chromatograms do not interfere with one another. A series of high-speed chromatograms are generated during one extraction, and the extraction and the chromatography are carried out simultaneously. Those chromatograms provide a fingerprint of the kinetics of the extraction process. Ensemble signal averaging provides a higher signal to noise ratio. Segmented signal averaging of a number of consecutive chromatograms generated from one extraction is similar to off-line fraction collection, but the speed of analysis is substantially enhanced.

This apparatus and the method disclosed herein provide quantitative analytical results without the requirement of exhaustive extraction.

DETAILED DESCRIPTION OF THE INVENTION

The invention is best understood by reference to the following description and appended claims with reference to the drawings wherein the parts are designated with like numerals throughout.

Figure 1:
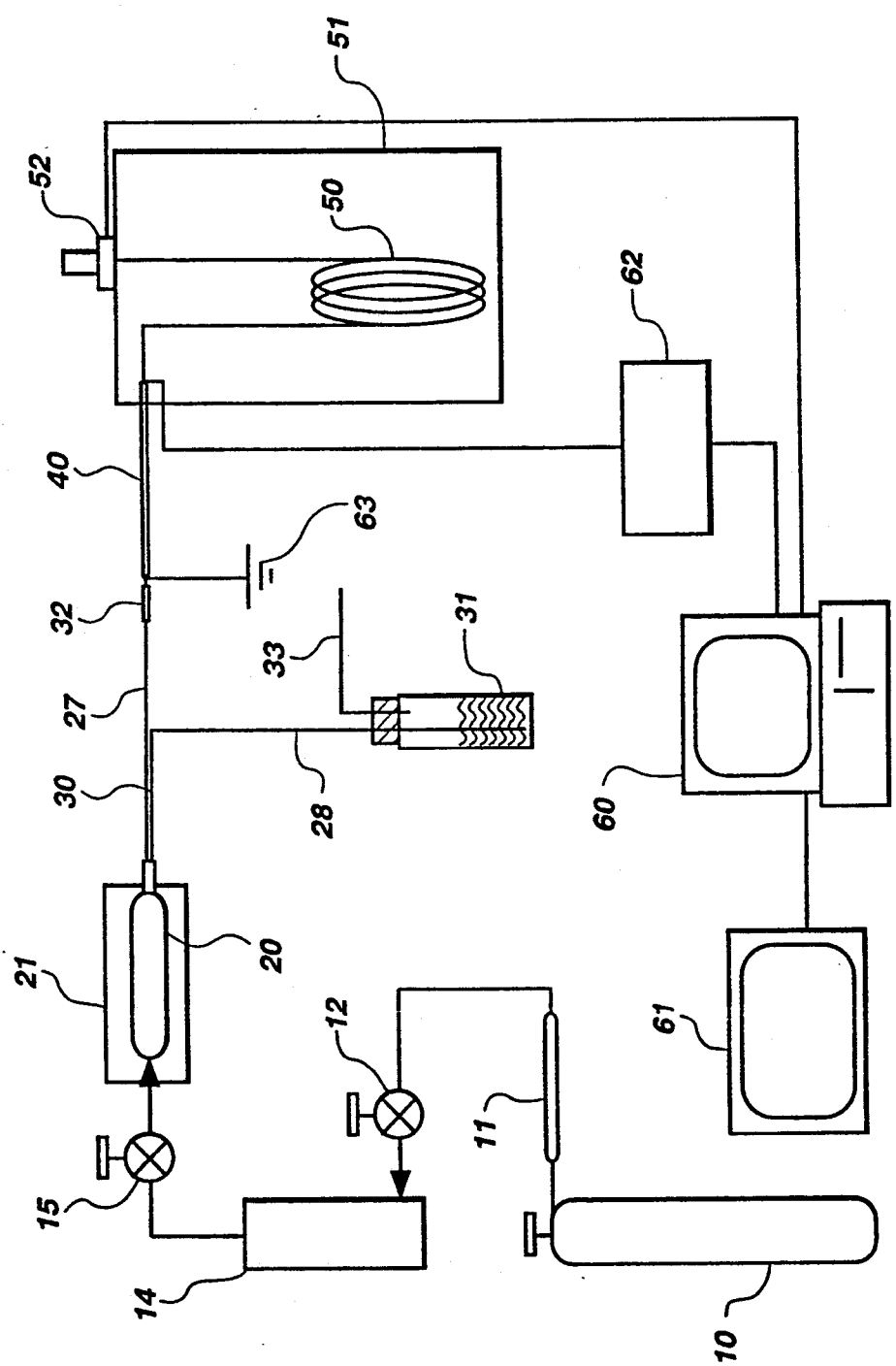
FIG. 1 is a schematic diagram of the apparatus used to carry out supercritical fluid extraction and gas chromatography simultaneously.

Referring to FIG. 1, there is illustrated a complete apparatus for the high-speed, thermally modulated SFE/GC system. Fluid delivery and/or electronic signal lines are not specifically referred to by number. The extraction system consists of a fluid supply tank 10, which is preferably SFE or at least SFC grade carbon dioxide. If the level of impurities in the $CO_2$ or other fluid supply is higher than what is acceptable, the fluid is further purified by an Alumina-C trap 11 and then passes through an on/off valve 12 to the high pressure pump 14. The fluid, When pressurized, passes through another on/off valve 15 and enters into the extraction cell 20 which is placed in a heating block 21 at constant temperature. Block 21 is made of aluminum or any other suitable material. The sample matrix is contained in extraction cell 20 and the extraction of analytes takes place in the extraction cell thereby producing an extractant which contains substances of interest dissolved in the $CO_2$ or other suitable SFE fluid. The extractant is then preferably split into two portions as it passes through a two-way flow restrictor 30. One of the two portions carried via a capillary tube 28 is bubbled into a solvent which is contained in a sample vial 31 and the expanded gases are then vented out through a venting capillary 33. The other extractant portion passes via tube 27 through a butt connector 32 which joins the restrictor 30 to a thermal desorption modulator 40

Figure 2A:
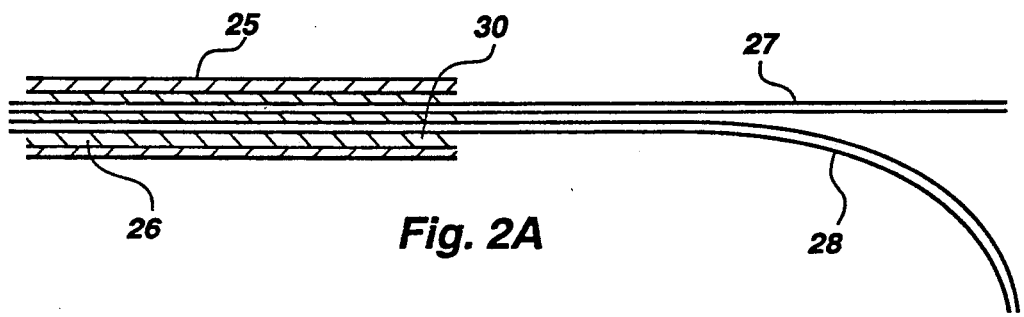
FIGS. 2A–C are expanded views showing embodiments of the two way flow restrictor and the thermal desorption modulator.

Referring now to FIG. 2A, the two-way flow restrictor 30 consists of two pieces of fused silica capillary, 27 and 28, which are preferably chemically deactivated, and a polyethylethylketone (PEEK) tube 25. The fused silica capillaries 27 and 28 are fixed into the PEEK tube tightly using an epoxy or other suitable resin 26.

Figure 2B:
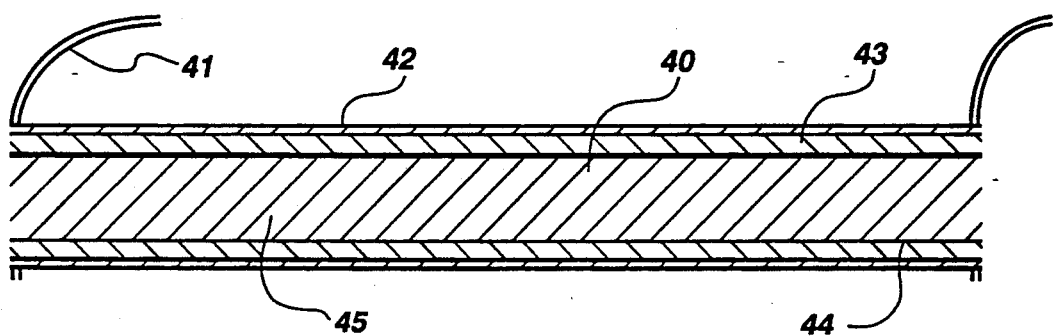

Referring now to FIG. 2B as well as FIG. the thermal desorption modulator 40, may be separate or may consist of the first portion of a gas chromatography absorption column 50. In either event, a uniform layer of electrically conductive paint 42 is applied on the outer surface of a measured length of the tubing or column 43 forming the modulator 40. The thickness of the layer 42 is selected based on the desired electrical resistance, which is preferably between 1 to 10 Ω. Two electrical leads 41 are wrapped on each end of the tubing 43, which is connected between a power supply 62 and ground 63 in FIG. 1. The column or tubing 43 of modulator 40, preferably, is a capillary column, which consists of a selected length of fused silica tubing having a layer of stationary phase 44 coated on the inner wall thereof. Extractant 45 (i.e. analytes from the matrix sample and SFE fluid) from the flow restrictor 27 passes through the modulator 40.

Figure 2C:
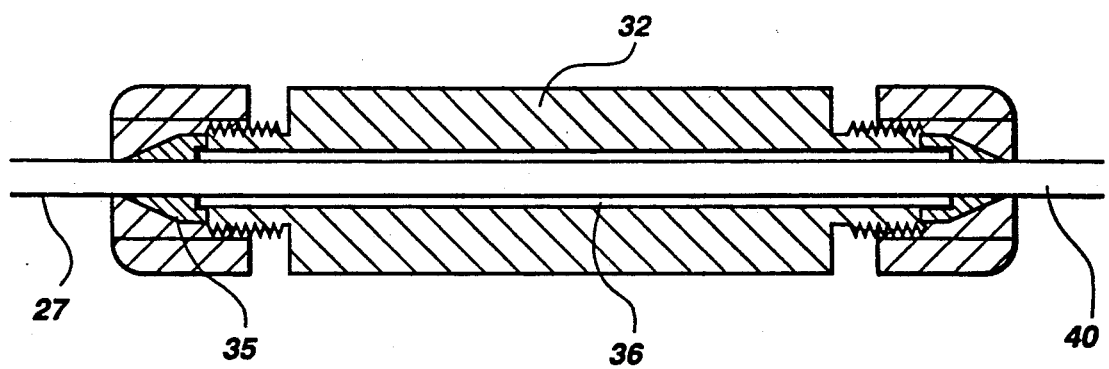

An expanded view of the connection 32 between the capillary tube 27 coming from column flow restrictor 30 and the modulator 40 is illustrated in FIG. 2C. This configuration is accomplished using a butt connector 32, graphite ferrules 35, and a fused silica sleeve 36. The sleeve must be deactivated and both ends should be sealed in the graphite ferrules.

In operating the thermal desorption modulator, a programmed analog signal from a computer 60 is used to control a power supply 62, which provides direct current at a defined level and duration to the modulator 40 through the electrical leads between the power supply 62 and ground 63.

The modulated sample substances entering the column 50, which is maintained at constant temperature in a chromatographic oven 51, are separated into individual components and detected by a gas chromatographic detector 52. The signal from the detector is then digitized and recorded by a microcomputer 60. A hard copy of the recorded signal can be obtained using a laser printer 61.

The invention, as described above with reference to FIGS. 1 and 2A-C, is a comprehensive apparatus and method of supercritical fluid extraction and gas chromatography utilizing a thermal desorption modulator as an interface between the two which allows for the simultaneous extraction and analysis of a sample obtained from either solid or liquid matrices. The supercritical state carbon dioxide or other suitable fluid is delivered at constant pressure e.g. with a syringe pump 14. Solid (or liquid) samples contained in the extraction vessel 20 are made to come in contact with the supercritical fluid. The mixture from the extraction vessel 20 contains analytes of interest dissolved in the supercritical fluid. This mixture preferably passes through a two-way restrictor 30, which splits the outlet flow from the extraction vessel into two fractions in lines 27 and 28. One of the two fractions is depressurized in a sample collection vial 31 for off-line analysis if necessary, and the other fraction is directed onto the interface, or the thermal desorption modulator 40, which can be either prepared on-column or prepared separately using different material from the analytical column 50 to achieve the desired selectivity. Extracted substances deposit onto the stationary phase 44 in the modulator when the supercritical fluid is depressurized to a gas and passes through the modulator 40 and then the analytical column 50. The ambient temperature of the modulator 40 can vary according to various applications. A thermal pulse is applied to the modulator 40 such as by passing an electrical current through the painted conductive layer 42 on the outside surface of the modulator 40. The retained substances are suddenly released from the modulator stationary phase as a short-band concentration pulse, which serves as an injection plug which is carried by the same extracting fluid (now as a gas) onto the analytical column 50 for subsequent separation. The separated sample bands are transduced to an electrical signal by a gas chromatographic detector 53 and an electrometer. The signal is then digitized and recorded as a function of time by a suitably programmed computer 60 or other comparable means.

The extractant from the extraction vessel is first split at flow restrictor 30 to meet the flow rate requirements for both extraction and chromatography. It turns out to be an advantageous feature in the sense that off-line sample collection (such as in vial 31) can be achieved simultaneously with SFE/GC analysis using the present invention. An appropriately designed two-way flow restrictor 30 is critical to the appropriate functioning of the system disclosed herein. It provides the means of flow splitting and the means of eliminating sample adsorption, which occurs when the sample substances come in contact with metal surfaces during depressurization such as when a tee is used in place of the two-way restrictor for the same purposes. The ratio of the split flow rates is selected based on the extraction and chromatographic configuration. Large extraction cells or large sample sizes usually require high flow rates for the extraction to proceed in a reasonab)e rate. The required flow rate through the analytical column, and the detection sensitivity, are also important factors to consider in selecting the flow split ratios. Various flow split ratios can be obtained by varying the dimensions of the two capillaries 27 and 28 in the two-way restrictor 30.

The two-way restrictor 30 consists of PEEK tubing 25 with a suitable dimension and two lengths of fused silica tubing 27 and 28. Preferably, the fused silica tubing is chemically deactivated. The two lengths of fused silica tubing 27 and 28 are fixed into the PEEK tubing 25 using epoxy resin 26.

Sample substances are ultimately transferred from the extraction cell 20 to the gas chromatographic column 50 by using a thermal desorption modulator 40 in the process disclosed herein. The modulator 40 is operated by using a computer controlled, programmable direct current power supply 62. The standing temperature of the modulator 40 is adjustable by applying a constant current to it. As previously explained, the temperature of the modulator 40 is maintained through resistive heating. The standing temperature is selected based on the properties of the analytes of interest. For example, for volatile substances, the standing temperature of the modulator 40 can be kept low such as at room temperature. For substances of lower volatility, a higher standing temperature is preferred to achieve efficient desorption.

The magnitude of the temperature pulses are controlled by the level of the applied electrical current through leads 41 to the conductive paint 42 and the current duration. The thermal pulses must be high enough to release most of the absorbed substances of interest from the modulator 40 Another consideration is the thermal stability of the absorbing material used in preparing the modulator. When a modulator is made directly on the capillary column, the absorbing material is simply the liquid stationary phase 44 coated on the inner wall. In this disclosed method, the modulator is preferably pulsed at fixed time intervals depending on the chromatographic retention times. A series of programmed, electrical signals from a computer 60 is used to actuate a power supply 62, which applies the required power to the leads 41 and conductive paint 42 of the modulator 40.

The modulator 40 can be made from various materials. However, two requirements must be met in order for it to properly function. The first requirement is that the material in the modulator must interact with analytes of interest either chemically or physically (e.g. absorptive or catalytic reactions). The second requirement is that a rapid concentration change must be generated by means of operating the modulator. As stated, the modulator used in this disclosed invention is a thermal desorption type. Absorption and desorption are controlled by manipulating the temperature of the modulator in the manner described.

The simultaneous operation of supercritical fluid extraction and gas chromatography are made possible by accelerating the separation process and by utilizing the thermal desorption modulator 40. It is therefore apparent that the thermal desorption modulator is the critical link to the successful operation of the system as described herein.

For proper operation of the gas chromatograph 50, a suitable length of capillary column with relatively small inner diameter is preferred to accomplish high-speed separations. A concentration pulse from the modulator 4 containing varying numbers of substances is separated by the column 50 into individual bands before the next concentration pulse is sent to the column 50. Throughout the extraction, both modulator 40 and column 50 operate simultaneously. The modulator 40 generates a series of concentration pulses at specified time intervals while the extraction proceeds, and the column 50 generates a corresponding series of chromatograms. The actual number of chromatograms for a run varies according to the total extraction time and the operating frequency of the modulator. All of these events are recorded in one data array in the memory of computer 60.

Data analysis is performed according to the information desired. However, the algorithm used may be determined by those skilled in the art and changed or modified from time to time according to variables such as sample size, cell volumes, supercritical fluid used, temperatures, flow rates, GC volume, etc. A more detailed description of data analysis is contained below.

DESCRIPTION OF SPECIFIC EMBODIMENT

Instrumentation. A schematic diagram of how the on-line SFE/GC system is used is shown in FIG. 1. A Varian 8500 high pressure syringe pump 14 with an internal cylinder volume of 250 mL was modified so that both pressure programming and control were achieved using an Apple II computer. SFC grade carbon dioxide (Scott Specialty Gases, Plumsteadville, PA) from tank 10 was used as the exstraction fluid. An alumina-C trap 11 was placed between the $CO_2$ tank 10 and the pump 14 to remove impurities. A 1-cm by 10-mm i.d. extraction cell 20, purchased from Upchurch Scientific (Oak, WA), which is commonly used in LC as a guard column was used. The extraction cell 20 was placed in a thermostated aluminum block 21. The temperature of this block was controlled from the control panel on the Hewlett Packard 5890 gas chromatograph (Injector A control line). The cell pressure was maintained constant by a two-way linear flow restrictor 30. The restrictor was constructed by cementing two lengths of fused silica capillary tubing 27 and 28 in a short section of PEEK tubing 25 (Upchurch Scientific, Oak, WA) with epoxy resin 26 (Epoxy Technology, Billerica, MA). The extractant 45 from the extraction cell was split between a collection vessel 31 and the thermal desorption modulator 40. The extraction fluid flow rate and splitting ratio could be adjusted by varying the dimensions of the two capillaries 27 and 28. The modulator 40 and the restrictor 30 were connected with a butt connector 32. As shown in FIG. 2C, a deactivated fused silica sleeve 36 was used inside the butt connector. Both ends of the sleeve were sealed in the graphite ferrules 35 so that the extracted analytes did not come in contact with the metal surface.

A thermal desorption modulator 40 was prepared at the head of an analytical column as reported by Liu et al., *J. Microl. Sep.* 1, 249-256 (1989). The electrically conductive paint 42 used to prepare the modulator was obtained from a local automobile parts store. The length of the modulator was 10 cm with a total electrical resistance of 1.7 Ω. The modulator was looped outside of the GC oven 51 at room temperature, and was operated by a programmable Model ATE-55-10M DC power supply 62 (Kepco, Flushing, NY).

A 1.2-m×50-μm i.d. fused capillary column with 0.25-μm SB-Biphenyl-30 stationary phase film was used as the analytical column 50 (Lee Scientific, Salt Lake City, UT). A flame ionization detector 52 on a Hewlett Packard 5890 gas chromatograph was used throughout this investigation. A DAS-16 A/D interface with 12 bits resolution (OMEGA Engineering, Stamford, CT) was used to digitize the signal. At large input range settings on the A/D interface, the signal was amplified with a low-noise preamplifier, Model SR560 (Stanford Research Systems, Sunnyvale, CA) to eliminate digitization noise.

Instrumental control, data acquisition, and data analysis were achieved using a DTK Keen-2530 computer 60. The computer software used was written in-house with Turbo-C compiler. The computer D/A output was used to program the DC power supply 62 so that the voltage applied to the modulator 40 could be selected from 0 to 50 volts with a maximum current output of 10 amperes. For this particular modulator and experimental setup, electrical pulses of 40 milliseconds in duration and 28 volts in magnitude at 10-s repetition intervals were used throughout the study. For sample substances with strong retention in the modulator stationary phase, longer pulses with greater magnitude should be used. The time intervals between pulses were selected according to the retention times of the analytes.

The data acquisition frequency was set at 20 Hz in the reported experiments. The program employed allowed the user to select different data frequencies from 0.0003 to 1000 Hz. Data display was achieved using Matlab-386 software (The Math Works, South Natick, MA).

Procedures. Supercritical fluid extractions were carried out at constant pressure in the dynamic extraction mode. Solid samples were packed into a 1-$cm^3$ cell 20, and placed in the thermostated heating block 21 at 50° C. for 10 min before introducing the extraction fluid into the cell. Since a valve was not used between the extraction cell 20 and the thermal desorption modulator 40, 10 seconds were required to pressurize the cell to a constant pressure level. This was determined by measuring the solute retention times in the first chromatograms generated until they became constant.

Data analysis was accomplished in the following manner. Three-dimensional SFE/GC plots were obtained by reshaping the row data array into a matrix. The dimensions of the matrix depended on number of chromatograms generated during the extraction. Curves showing the SFE profiles of the selected components were measured from the original data array. The retention times of the selected components were measured from signal averaged chromatograms. Then, SFE curves were obtained for each compound by sampling data at the respective retention times of the compounds from the data array. The $\ln(m/m_o)$ versus time plots were generated by computing signal averaged chromatograms from the data array. Usually, the data array was first divided into three segments and a signal averaged chromatogram was obtained from each segment, which represented the amounts of analytes extracted in that time period. The total amounts of analytes present in the original sample matrix were determined using the following Equation 1:

$$m_o = m_1 + m_2^2/(m_2 - m_3). \quad (1)$$

where, $m_o$ is the amount of analyte in the original sample matrix, $m_1$ is the amount of analyte extracted within time $t_1$ during which the first data segment was generated, and $m_2$ and $m_3$ are the amounts of analyte extracted within the following two time periods. These three quantities can be obtained using the signal averaged chromatograms described above. After $m_0$ was obtained, a $\ln(m/m_0)$ versus time plot was generated by signal averaging different numbers of chromatograms in the set from the start of the SFE/GC analysis.

In obtaining calibration curves, known amounts of sample substances were dissolved in methylene chloride and spiked into the extraction cell 20 which was packed with soil that had previously been extracted with aoetonitrile. Before the analytes were spiked, the soil matrix was further extracted with neat $CO_2$ at 300 atm for 6 h. The extraction was carried out with neat $CO_2$ as extraction fluid at 200 atm and for 20 min. The two-way restrictor 30 had one capillary 28 with dimensions of 25 cm×13-μm i.d. to the collection vessel 31 and a second capillary 27 with dimensions of 15 cm×10-μm i.d. to the thermal desorption modulator 40. The split ratio was 1:82 (0.4 mL min$^{-1}$ to the column, and 33 mL min$^{-1}$ to the collection vessel, measured as $CO_2$ gas). The GC column 50 was maintained at 140° C. isothermal. The detector temperature was 350° C. Data analysis was carried out in the same manner as described above. At each concentration level, $m_0$ was computed and plotted against the spiked concentration.

Sample preparation. The soil used to prepare samples was first extracted with acetonitrile in a Soxhlet apparatus. Before the analytes were spiked, the soil was further cleaned by extracting with $CO_2$ at 300 atm for 6 h. The PAH spiked soil samples were prepared by dissolving PAH standards in methylene chloride (Spectral grade from Fisher Scientific) at approximately 1 mg mL$^{-1}$ concentration. The clean soil was swirled with methylene chloride and the standard solution was added. The solvent was evaporated by purging with nitrogen gas for 24 h. A soil sample containing toluene, p-xylene, and benzylamine was obtained by a vapor absorption method. A capillary (3 cm×1-mm i.d.) containing a mixture of these three compounds was sealed in a sample vial which contained 100 g of soil. The sample vial was maintained at room temperature until the compounds in the capillary were completely evaporated.

Figure 3:
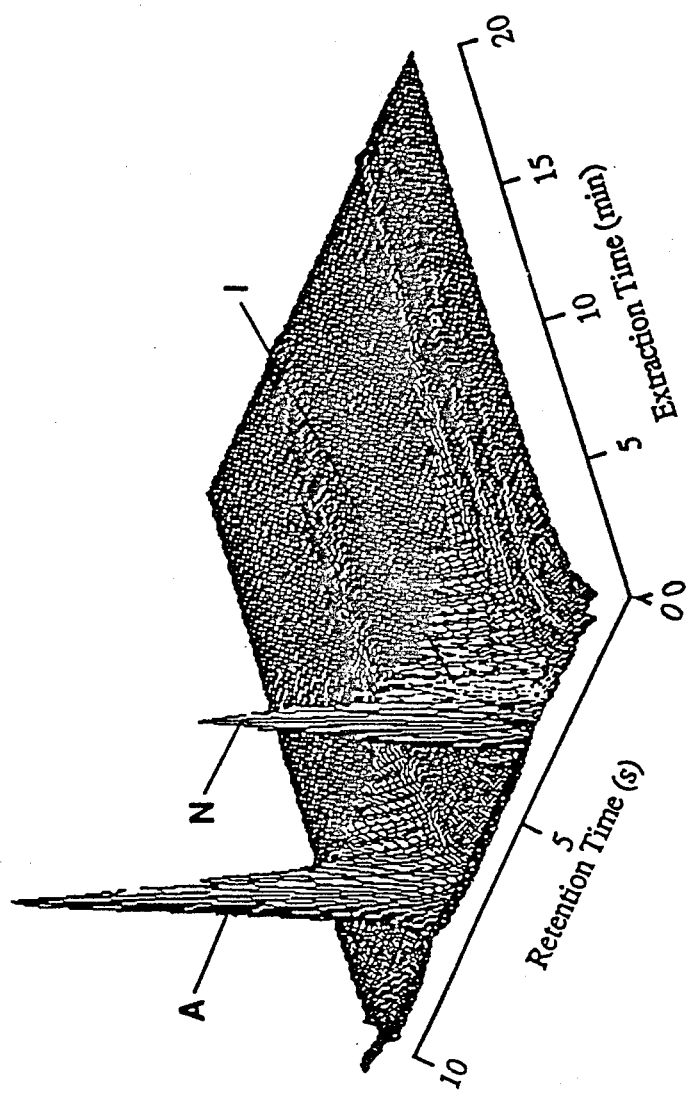
FIG. 3 is a three dimensional representation of the SFE/GC analysis of a soil sample spiked with indent, naphthalene, and acenaphthene obtained using the apparatus and system diagrammed in FIG. 1.

FIG. 3 shows a three-dimensional representation of an SFE/GC analysis of an indent, naphthalene and acenaphthene spiked soil sample using supercritical carbon dioxide as the extracting fluid By using the disclosed invention, real-time monitoring of a dynamic supercritical fluid extraction process was achieved Extraction was accomplished in an extraction cell under the following conditions: dynamic extraction with $CO_2$ at 50° C. and 200 atm, 0.8410-g sample in 1-cm×10-mm i.d. extraction cell. A thermal desorption modulater was operated as follows: 28V DC electrical pulses of 40-ms duration were applied at 10-s repetition intervals. Finally, a high-speed GC column was utilized under the following conditions oven temperature at 140° C., 1.2-m×50-μm i.d. column with 0.25-μm stationary phase film, $CO_2$ carrier gas at 0.4 mL min$^{-1}$. The data acquisition frequency was 20 Hz. The compounds shown in FIG. 3, in order of increasing retention time, are indene, naphthalene, and acenaphthene.

In FIG. 3, one axis gives the extraction time (in minutes), and the other axis gives the retention times (in seconds) of the components in the high-speed chromatograms. Since a chromatogram was generated every 10 seconds in this example, 120 chromatograms were generated during 20 minutes extraction time. The extraction sequence of each individual component can be monitored simultaneously. As is shown in FIG. 3, an early eluting compound such as indene (I) in this soil matrix, has a higher vapor pressure or greater solubility in supercritical carbon dioxide. Therefore, its concentration maximum in the extractant appeared earlier than naphthalene (N) and acenaphthene (A).

Figure 4:
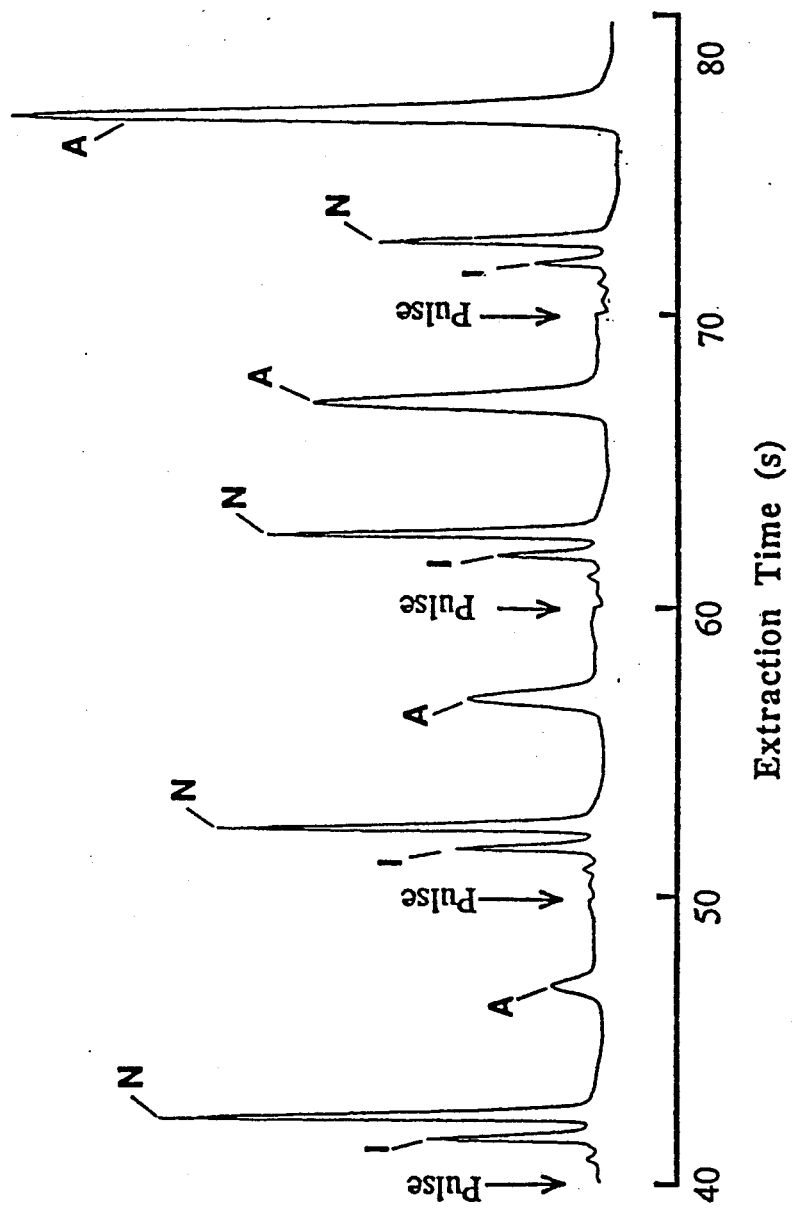
FIG. 4 is a series of high-speed chromatograms sampled during the same SFE/GC run as shown in FIG. 3.

The relative rates of extraction for different compounds can be further clarified by measuring the individual chromatograms during the SFE/GC run. FIG. 4 shows sampled chromatograms from 40 to 80 seconds from the start of the extraction. The extraction, chromatography, and modulation conditions, and sample composition were the same as shown in FIG. 3. Four consecutive chromatograms were plotted in the figure During this time period, the concentrations of both indene (I) and naphthalene (N) in the extractant were decreasing, but the concentration of acenaphthene (A) was increasing, which can be seen clearly by comparing the peak sizes for the components in the chromatograms.

Figure 5:
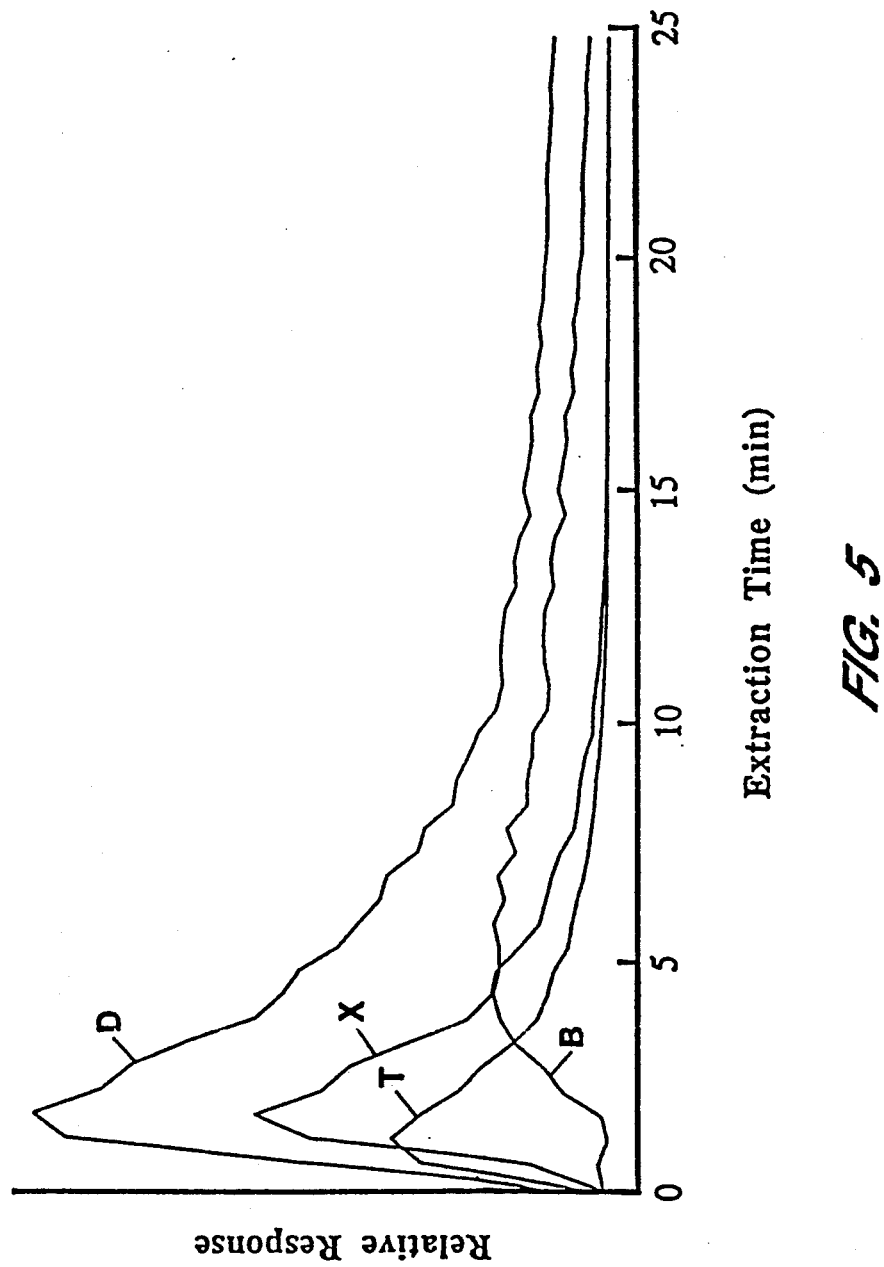
FIG. 5 represents dynamic supercritical fluid extraction profiles obtained for the analysis of a spiked soil sample [(a) toluene, (b)p-xylene, (c) benzylamine, and (d) total SFE profile]using the system and method as disclosed herein.

FIG. 5 shows the real-time, simultaneous monitoring of the SFE profiles of toluene, p-xylene and benzylamine in soil. SFE profiles were determined by monitoring each individual high-speed chromatogram during an SFE/GC run. Extraction conditions were as follows: dynamic extraction with $CO_2$ at 50° C. and 250 atm, 1.0-cm$^3$ extraction cell. Modulator and modulation parameters were the same as in FIG. 3. High-speed GC was carried out using the same column as used in FIG. 3 with an oven temperature at 110° C. Compound profiles identified in FIG. 5 are toluene (T), p-xylene (X), and benzylamine (B), and the total SFE profile (D). As expected, there is little difference in solubility and solvating rate for toluene (T) and p-xylene (X) in supercritical $CO_2$. The SFE profiles of these two compounds are quite similar. However, benzylamine (B) followed a very different extraction profile. A longer time is required for this compound to reach its dissolution equilibrium in the fluid, and its concentration maximum appeared approximately 1.5 minutes later than the other two components Since benzylamine has a greater polarity and stronger interaction with the matrix as compared to toluene and p-xylene, a slower mass transfer from the matrix into the extraction fluid was expected. This fact caused a slower decay in the concentration profile after the maximum For analytical purposes the exponential behavior of the extraction profile after the concentration maximum opens up the possibility of extrapolation to obtain quantitative analytical information in a shorter time than would be required for exhaustive extraction. A theoretical model can be adopted to obtain quantitative results Using the apparatus illustrated in FIGS. 1 and 2A-C and the method disclosed herein, the total analysis time can be substantially reduced as compared to the prior art in this field.

Figure 6:
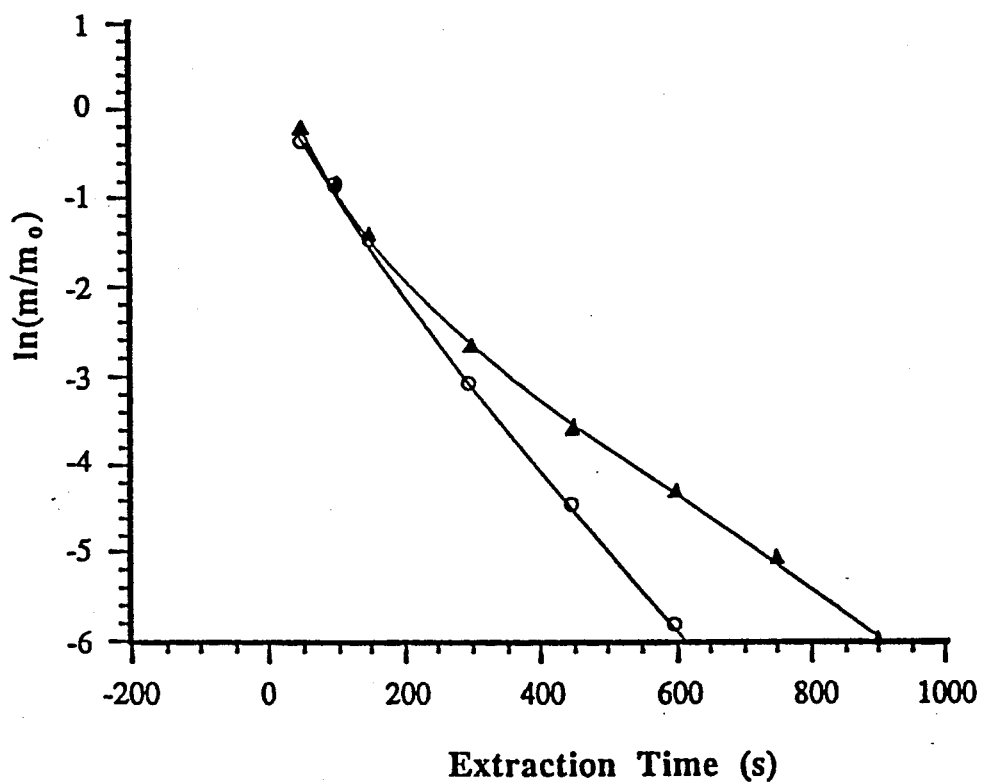
FIG. 6 is a plot of $\ln(m/m_o)$ versus extraction time, (s), for the extraction of toluene and p-xylene from soil, which shows the obtaining of quantitative analytical results using the disclosed method. The top curve is for toluene and the bottom curve is for p-xylene.
Figure 7:
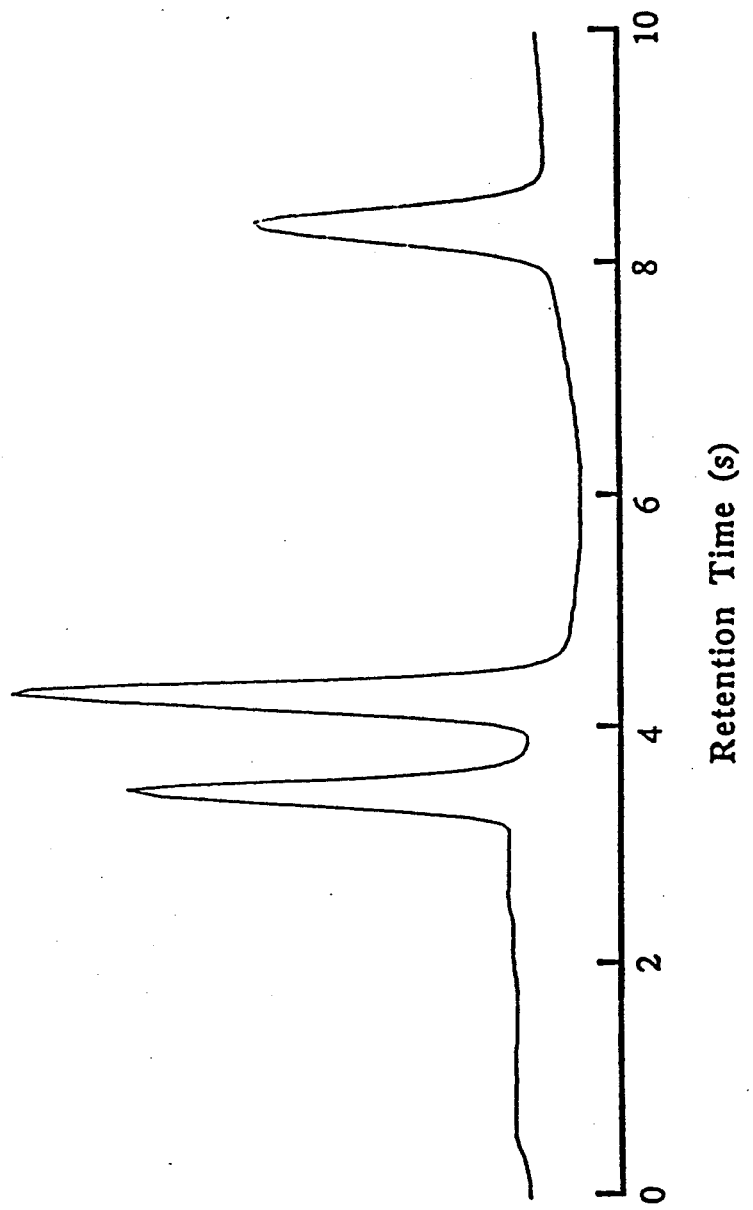
FIG. 7 shows the signal averaged chromatogram from 40 consecutive chromatograms generated from 50 to 450 seconds during the extraction used for the calculation of FIG. 6 in obtaining quantitative results.

FIG. 6 shows the $\ln(m/m_0)$ versus time plot for the extraction of toluene and p-xylene from soil. To generate this plot $m_0$ was obtained using equation 1 by computing the signal averaged chromatograms over three different time intervals during the run, and m was obtained by computing signal averaged chromatograms over various time periods during the extraction. FIG. 7 is a signal averaged chromatogram used for the calculation of FIG. 6 in obtaining quantitative results.

As indicated in Equation 1, $m_0$ can be computed using different time intervals for $m_1$, $m_2$, and $m_3$. A measurement was made to see if the calculated value was affected by using various time intervals. The results are given in Table I. All calculated results for toluene (T) and p-xylene (X) are very close to each other, with relative standard deviations (RSD) of 0.13 and 0.38, respectively. Since the non-linear region for benzylamine (B) lasts about 230 seconds (see FIG. 5), The selected time interval for $m_1$ must be long enough to cover this region. As shown in Table I, greater deviation for $m_0$ values were generated for benzylamine when $\Delta t_1$ was 200 seconds, which is shorter than the non-linear region of the $\ln(m/m_0)$ versus time plot. Basically, the calculated $m_0$ values were not affected by using various time intervals if the selected $\Delta t_1$ covers the entire non-linear region in the $\ln(m/m_0)$ versus time plot.

TABLE I

| Effect of Time Interval Used in Computing $m_0$ | | | | | |
|---|---|---|---|---|---|
| time intervals used (s) | | | measured value of $m_0$ (arbitrary units) | | |
| $\Delta t_1$ | $\Delta t_2$ | $\Delta t_3$ | T | X | B |
| 0–200 | 200–400 | 400–600 | 116 | 196 | 251 |
| 0–400 | 400–600 | 600–800 | 116 | 196 | 279 |
| 0–400 | 400–800 | 800–1200 | 116 | 197 | 266 |
| 0–300 | 300–800 | 800–1300 | 116 | 197 | 262 |
| 0–300 | 300–700 | 700–1100 | 116 | 196 | 263 |
| 0–500 | 500–1000 | 1000–1500 | 116 | 198 | 262 |
| mean on $m_0$ | | | 116 | 197 | 266* |
| Standard deviation (SD) | | | / | 0.82 | 7.2. |
| RSD % | | | / | 0.42 | 2.7. |

*data were calculated without using the first time interval example.

Although the invention has been described and illustrated with reference to specific embodiments, those trained in the at will recognize that modifications and alterations may be made without departing from the principles of the invention as described hereinabove and as set forth in the following claims.

We claim:

1. A method for conducting simultaneous on-line supercritical fluid extraction and chromatographic analysis of one or more organic species of interest from a sample matrix comprising;
   (a) providing in sequence, a supercritical fluid extraction cell, a thermal desorption modulator and a heated gas chromatography column; said system also containing a supercritical fluid source, pump means for directing the flow of supercritical fluid through said system, heating means for applying heat to said thermal desorption modulator at regulated time intervals, detection means for detecting bands eluted from said gas chromatography column at regulated time intervals, means for transducing said detected bands into electrical signals, and processing means for receiving, processing and displaying said signals as analytical results;
   (b) directing supercritical fluid from said fluid source to said extraction cell containing said matrix sample at a constant pressure via said pump means thereby forming an extractant in said cell consisting of said organic species dissolved into said supercritical fluid;
   (c) passing said extractant into said thermal desorption modulator, maintained at a minimum standing temperature by said heating means, under reduced pressure where the organic species are retained as a deposit onto a stationary phase in said modulator and said supercritical fluid as a gas passes through said modulator to said analytical column;
   (d) applying additional heat at regulated time intervals to said modulator whereby the retained organic species are suddenly released from said stationary phase of said modulator as a shortband concentration pulse,
   (e) injecting said short-band concentration pulse containing said organic species into said heated gas chromatography column by means of said supercritical fluid gas where said organic species are separated into detectable bands;
   (f) detecting said bands by said detection means at regulated time intervals as chromatograms and transducing said chromatograms to electrical signals; and
   (g) digitizing and recording said electrical signals, as a function of time, by said processing means into displayable analytical results.

2. A method according to claim 1 wherein said system contains a two way flow restrictor positioned between said extraction cell and said thermal desorption modulator to further control the pressure within said extraction cell and wherein the extractant from said extraction cell is split by an on-line conduit and an off-line conduit at said flow restrictor into a first on-line stream and a second stream off-line stream with said first on-line stream passing through said on-line conduit to said thermal desorption modulator and said second off-line stream passing through said off-line conduit to collection means for removal from said system.

3. A method according to claim 2 wherein said thermal desorption modulator is a column and said heating means for maintaining the standing temperature and applying additional heat to said thermal desorption modulator at regulated time intervals is a uniform layer of a electrically conductive paint having an electrical resistance between about 1 to 10 $\Omega$ applied on a measured portion of the outer surface of said column, said paint being connected at either end of by electrical leads which are connected between a variable power supply source and ground.

4. A method according to claim 3 wherein, in heating said thermal desorption modulator, a programmed analog signal from said processing means is used to control said power supply source to provide an applied direct electrical current at a defined level and duration to said modulator through said electrical leads between said power supply source and ground.

5. A method according to claim 4 wherein said thermal desorption modulator is maintained at a minimum standing temperature by applying a minimum constant current to said modulator, said standing temperature being based on the properties of the organic species of interest.

6. A method according to claim 5 wherein said additional heat is applied to said thermal desorption modulator at regulated intervals to generate temperature pulses in said modulator, the magnitude of which are controlled by the level and duration of the applied direct electrical current.

7. A method according to claim 6 wherein the temperature pulses are generated at fixed time intervals depending upon the retention times of the organic species of interest in the chromatography column.

8. A method according to claim 7 wherein the time interval between temperature pulses is fixed to allow the organic species of interest to be separated by the gas chromatography column into individual bands and detected before the next temperature pulse is applied to said modulator.

9. A method according to claim 8 wherein the series of temperature pulses generated at specified time intervals in the thermal desorption modulator during the extraction process corresponds to the number of chromatograms generated in said chromatography column.

10. The method according to claim 9 wherein the actual number of thermal pulses and chromatograms generated for any specific organic species of interest varies according to the total extraction time.

11. The method according to claim 3 wherein the extractant split at said flow restrictor into said first on-line and second off-line streams results in streams whose flow rates and ratios are selected based on the extraction and chromatographic configuration of the system.

12. The method according to claim 11 wherein the desired relative flow rates and ratios of said first and second streams are obtained by varying the dimensions of the on-line and off-line conduits in said two-way restrictor.

13. A system for conducting simultaneous on-line supercritical fluid extraction and chromatographic analysis of one or more organic species of interest from a matrix sample comprising in sequence;
   (a) a supercritical fluid extraction cell,
   (b) a thermal desorption modulator; and
   (c) a heated gas chromatography column
   (d) said system also containing (i) a supercritical fluid source, (ii) pump means for directing the flow of supercritical fluid from said source through said system, (iii) heating means for applying heat to said thermal desorption modulator at regulated time intervals, (iv) detection means for detecting bands eluted from said gas chromatography column at regulated time intervals, (v) means for transducing said detected bands into electrical signals, and (vi) processing means for receiving, processing and displaying said signals as analytical results.

14. A system according to claim 13 which further contains a two way flow restrictor positioned between said extraction cell and said thermal desorption modulator, comprising means for receiving extractant from said extraction cell and dividing said extractant by containing an on-line conduit and an off-line conduit, said on-line conduit being in communication with said thermal desorption modulator and said off-line conduit being in communication with the collection means for removal of extractant from said system.

15. A system according to claim 14 wherein said thermal desorption modulator is a column and said heating means for maintaining the standing temperature and applying additional heat to said thermal desorption modulator at regulated time intervals is a uniform layer of an electrically conductive paint having an electrical resistance between about 1 to 10 $\Omega$ applied on a measured portion of the outer surface of said column, said paint being connected at either end by electrical leads which are connected between a variable power supply source and ground.

16. A system according to claim 15 wherein said thermal desorption modulator is heated by application of a direct electrical current at a defined level and duration to said modulator through said electrical leads between said power supply source and ground by means of a programmed analog signal from said processing means to control said power supply source.

17. A system according to claim 16 wherein said thermal desorption modulator is maintained at a minimum standing temperature by application of a minimum constant current to said modulator.

18. A system according to claim 17 wherein said additional heat applied to said thermal desorption modulator at regulated intervals to generate temperature pulses in said modulator is controlled by means of the level and duration of the applied direct electrical current.

19. A system according to claim 18 wherein the level and duration of the applied direct electrical current to said modulator is at fixed time intervals.

20. A system according to claim 19 wherein said fixed time intervals are regulated to coincide with the detection of separated bands in the gas chromatography column by said detecting means.

21. The system according to claim 14 wherein the diameters of said on-line conduit and said off-line conduit are selected based on the extraction and chromatographic configuration of the system.

22. The system according to claim 21 wherein the diameters of said on-line conduit and said off-line conduit are varied to provide for the desired relative flow rates and ratios through said two-way flow restrictor.

* * * * *